United States Patent
King et al.

(10) Patent No.: US 9,999,342 B2
(45) Date of Patent: Jun. 19, 2018

(54) SINGLE POWER SWITCH FOR MODULAR MEDICAL IMAGING SYSTEM

(71) Applicant: Karl Storz Imaging, Inc., Goleta, CA (US)

(72) Inventors: Timothy King, Goleta, CA (US); Ralph Fuquay, Santa Barbara, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 1244 days.

(21) Appl. No.: 13/731,705

(22) Filed: Dec. 31, 2012

(65) Prior Publication Data

US 2014/0184767 A1    Jul. 3, 2014

(51) Int. Cl.
*A61B 1/00* (2006.01)
*A61B 1/045* (2006.01)

(52) U.S. Cl.
CPC ...... *A61B 1/00016* (2013.01); *A61B 1/00036* (2013.01); *A61B 1/00105* (2013.01); *A61B 1/045* (2013.01); *A61B 1/00059* (2013.01)

(58) Field of Classification Search
CPC ... A61B 1/00016; A61B 1/00; A61B 1/00036; A61B 1/00105; A61B 1/00059; H04N 21/23439
See application file for complete search history.

(56) References Cited

U.S. PATENT DOCUMENTS

| 2003/0093503 | A1* | 5/2003 | Yamaki | G06F 19/3406 709/220 |
| 2006/0068834 | A1* | 3/2006 | Jones | A61B 8/00 455/550.1 |
| 2008/0100699 | A1 | 5/2008 | Hibi | |
| 2008/0225134 | A1* | 9/2008 | Amling | A61B 1/00119 348/222.1 |
| 2010/0295870 | A1* | 11/2010 | Baghdadi | G09G 5/005 345/650 |

FOREIGN PATENT DOCUMENTS

JP    3559593 B2    9/2004

OTHER PUBLICATIONS

European Search Report Application No. EP 13 19 7987 Completed: Apr. 4, 2014; dated Apr. 11, 2014 6 pages.
European Office Action Application No. 13197987.4 dated Oct. 9, 2017 5 Pages.

* cited by examiner

*Primary Examiner* — David N Werner
*Assistant Examiner* — Berteau Joisil
(74) *Attorney, Agent, or Firm* — Michael Joseph Loi

(57) ABSTRACT

A modular video imaging system, and more particularly, a modular video imaging system having a control module connectable to multiple input modules. The control module and each input module having its own power supply and the input modules each capable of receiving differing types of image data from different types of cameras and processing the image data into a format recognizable by the control module. The control module controlling the ON/OFF condition of the input modules, such that each input module can be connected and disconnected during use.

20 Claims, 6 Drawing Sheets

SINGLE POWER SWITCH FOR MODULAR MEDICAL IMAGING SYSTEM

FIELD OF THE INVENTION

The invention relates to a modular medical imaging system having a control module connectable to a variety of input modules and, more in particularly, the invention relates to a modular system where the power for the input modules is controlled by the control module.

BACKGROUND OF THE INVENTION

The field of endoscopy, to which the present invention relates, includes medical diagnostic and therapeutic disciplines that utilize endoscopes to view otherwise inaccessible body cavities using minimally invasive surgical procedures. Endoscopes typically include cameras located at the distal tip of the endoscopes to capture images. Endoscopic cameras are typically small and lightweight for ease of use by medical professionals.

In known systems, endoscopic cameras are typically connected to a Camera Control Unit ("CCU"), with the CCU processing and displaying the imaging data transmitted from the endoscopic camera. Often, different medical procedures require different camera types, leading to a large inventory of cameras. Additionally, each camera type must be compatible with the CCU to function correctly. As such, each CCU has software to process and operate a variety of camera technologies, and as new technologies become available, the CCU may need updated software to properly process images from new camera technology. Additionally, often the CCU hardware becomes outdated, thus requiring an entirely new CCU to process the images of both old and new camera technologies used by a physician.

CCUs may be designed to be reprogrammable and reconfigurable, and as such, an older model CCU may sometimes be upgraded or configured to work with a new camera technology. However, in many cases the older model CCU may be too outdated to update or it may be less costly to replace the older model CCU with a new one because the reconfiguring of the CCU is often a time and labor intensive process that requires the CCU be returned to the manufacturer for disassembly, installation of new components and testing. Moreover, while it may be possible to update software in older model CCUs, the existing hardware in older model CCUs may not allow for the older model CCUs to support software for newer technology image sensors and image formats provided with newly developed camera technology.

In known systems, endoscopic cameras used during endoscopic surgery are typically referred to as heads or camera heads. To achieve the desired size and weight of the camera heads, camera head and/or integrated endoscope-camera assembly electronics are typically separated physically from the majority of circuitry required to process and output high-quality, color video images. The endoscope-camera assembly electronics is typically housed in the CCU. In known systems, CCUs may be placed on or in carts, in or on ceiling boom arms, or may be permanently wall-mounted.

In known video imaging systems, a cable simply connects a camera head to a CCU. When image data is acquired, or picked up, it is sent by the camera head to the CCU through the cable. Upon receiving the image data from the camera head, the CCU processes the signal and displays the acquired image on a viewing device. Generally, the image is used by a medical professional and/or for storage on various media (video cassette recorder, floppy disk, hard drives, flash drives, compact disks, digital video disks, and the like) and/or for transmission to remote locations in various manners, such as by the Intranet, Internet, radio transmission, and the like.

The CCU may also send commands to the camera head to adjust various settings (i.e. color balance, electronic shutter for light sensitivity, and other optical and electronic characteristics).

Traditionally, CCUs are compatible with a limited number of camera heads. A CCU's hardware is usually difficult to configure for proper communication with varying types of camera heads because camera heads use varying types of imaging devices that can differ in pixel resolution, timing requirements (i.e. PAL, NTSC, Progressive, and other formats), signal output type (i.e. analog or digital), physical size, and in other characteristics.

Analog video system types differ in scanning principles, resolution capability, sampling rates, aspect ratios, synchronization, bandwidth, and the like. Moreover, video system types may differ between broadcast, closed circuit, and computer applications. Analog video systems are typically classified as either composite (luminance and chrominance components multiplexed into a single signal) or component (separate signals for each chrominance component, and synchronization signals). In broadcasting applications, composite formats are generally used. For closed circuit systems (such as video production and editing, medical, industrial, and scientific applications) component formats are typically used. The primary composite analog video standards used are primarily PAL, NTSC, and SECAM, with one specific standard used in different geographical areas.

Digital video systems are typically differentiated by their application. Advanced television (ATV), high definition television (HDTV), and computer systems may differ in format and signal characteristics. In some areas, digital video formats and standards are currently being developed and adopted. The Society of Motion Picture and Television Engineers (SMPTE) normally defines and adopts voluminous digital video formal standards. As each is adopted, various applications, and application improvements generally will also be realized. Some digital video standards currently in use are: IEEE-1394 FireWire®, ISO/IEC IS 13818, International Standard (1994), MPEG-2, and ITU-R BT.601-4 (1994) Encoding Parameters of Digital Television for Studios.

Furthermore, there may be variability from device to device of the same type, which may affect camera head performance. Additionally, commands sent from the CCU to the camera head are generally unique depending upon the camera head type being used. Moreover, as repairs, modifications, or improvements are made to camera heads, the CCU, which was originally designed to be compatible with the older camera head, may become incompatible and may require upgrading as well.

This overall variability in camera heads, either caused by imaging device technologies or by CCU command characteristics, often results in a CCU being specifically designed to be compatible with a specific camera head type. Also, consumers may desire different capabilities related to specific applications of the cameras, such as medical, industrial, and scientific uses. Capabilities include picture in picture (PIP), reverse video (image flip), electronic zoom, electronic rotation, still image capture, and stereoscopic video interface.

Moreover, CCUs are typically designed for use with camera head technologies currently in existence, and not designed to anticipate and accommodate camera heads yet to be developed. Hence, CCUs are typically not designed to be compatible with future camera head technologies; particularly, image device and image signal transmission technologies. These differences between older and newer camera heads also contribute to compatibility problems.

Because CCUs are usually compatible with limited quantities of camera heads, CCUs are typically discarded in favor of ones that were designed concurrently and/or to be compatible with particular camera head technologies. Consequently, CCUs have become an added expense often associated with changing imaging devices or camera heads. Further, it is typically desired for camera heads to be improved due to the demand from consumers to have the latest technology and advancements in equipment. Moreover, CCUs used in medical and veterinary fields are increasingly being mounted permanently in equipment bays or carts and/or permanently mounted within the walls of surgical operating rooms themselves. The expense associated with replacing CCUs to maintain compatibility with camera heads is subsequently passed onto consumers.

Thus, there exists a need for a modular imaging system that overcomes the disadvantages of the prior art. There exists a need to provide a system having a control module connectable to multiple input modules that may be connected to various camera heads and that may receive data in various formats from various camera heads. There exists a need for the input module to be connected to a control module that may be updated or reprogrammed in an efficient and cost effective manner, rather than replacing the older input module or control module with a newer module. There exists a need for the modular imaging system, including at least one input module and a control module, to be readily compatible with existing and future imaging technologies and that allows for the at least one input module and the control module to be backwards and forwards compatible.

It is also desired to control the power state of the input modules via the control module upon connection of the modules. It is also desired for each module to have its own power supply. Furthermore, it is desired that the input modules default to a powered on state when disconnected from the control module, allowing the modules to be connected and disconnected without powering down. Finally, it is desired that the input modules are able to be connected and disconnected from the control module during use without the input module resetting or powering down.

SUMMARY OF THE INVENTION

Accordingly, it is an object of the invention to provide a modular medical video imaging system having a control module in signal communication with at least one input module. Both the control module and the at least one input module having and on condition and an off condition. The at least one input module being in the on condition when the input module receives an on signal indicating the control module is in the on condition and the at least one input module being in the off condition when the at least one input module receives a off signal indicating the control module not in the on condition.

The at least one input module may have a disconnected state from the control module where the at least one input module defaults to the on condition.

The control module and the at least one input module may be connect by a cable including a first set of wires allowing for image data to be transmitted across the cable and a second set of wires for the on signal and the off signal to be transmitted across the cable.

The control module and the at least one input module may be connected wirelessly.

The control module may further have a power switch with an on position and an off position. The power switch controlling one or more power supplies in the control module and the at least one input module.

Still further, the one or more power supplies of the control module and/or input module may be capable of powering other devices such as light sources, endoscopes or other medical equipment.

It is also an object of the invention to provide a modular medical video imaging system having a control module with an on condition and an off condition and at least one input module having an on condition and an off condition. The control module and the at least one input module capable of being connected and disconnected from each other. The control module sending a control signal the at least one input module the at least one input module is connected to the control module, the control signal communicating to the at least one input module whether the control module is in the on condition or the off condition. The at least one input module receiving the control signal and being in the on condition when the control signal indicates the control module is in the on condition and the at least one input module being in the off condition when the control signal indicates the control module is in the off condition. Still further, the at least one input module being in the on condition when the at least one input module is disconnected from the control module.

The at least one input module may be disconnected and connected to the control module when the control module is in the on condition without the at least one input module entering the off condition.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1A:
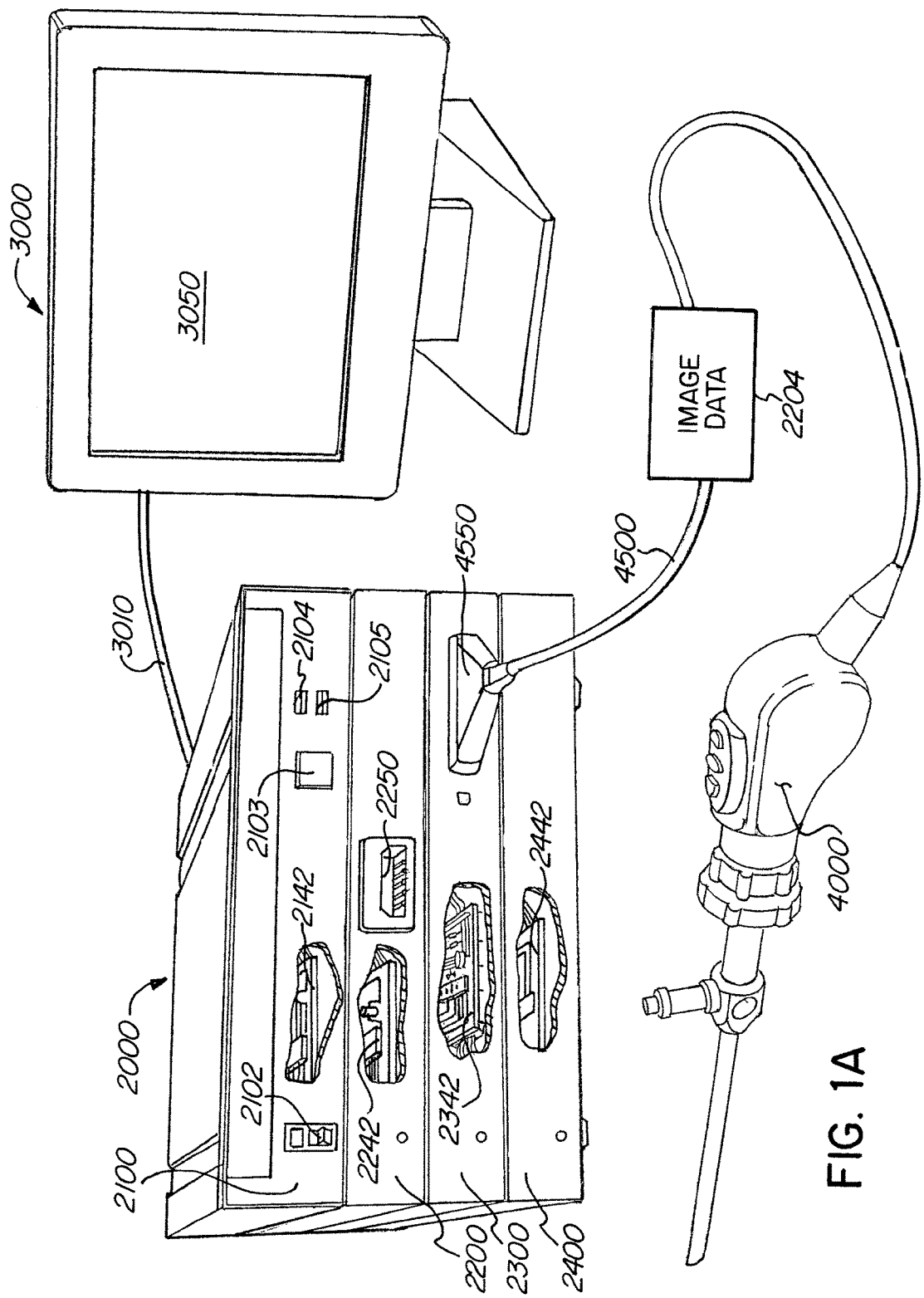
FIG. 1A is a perspective view of the front of an embodiment of the invention.

Accordingly, the invention involves a modular medical imaging system including several modules, such as an input module and a control module, which can be developed, sold and installed at different times. For example, a system may be initially installed with a control module and several input modules, and later additional modules can be added to the system.

The system allows for later developed modules incorporating various technologies and evolving industry standard interfaces as they evolve into an endoscopic system. By having modularity between the control module and input module, manufacturers can prevent having to re-design an entire new system for newer technologies and end users can avoid purchasing entirely new systems. The system provides the ability to accommodate future imaging system improvements and adaptations as current technology limitations are overcome by adding new input modules, which are forward and backward compatible with the control module, without obsolescing initial customer investments in control modules. The system also provides the ability for a user to add a new control module to accommodate future improvements, which is forward and backward compatible with older input modules. This allows one to take advantage of new features and functions of one module without requiring redesign and/or replacement of the entire system.

For example, the industry standard in display and recording infrastructure technologies evolve at a different rate than, say, the video endoscope technology, imaging technology, or proximal camera head technology. Newer technologies often use differing imaging data and parameters, such as aspect ratio, timing, pixel rate, pixel resolution, and pixel encoding. By having an input module connected to a control module, where the input module is forward and backward compatible with the control module, new camera technologies may be provided to replace outdated camera technologies, while still being compatible with older control modules.

Thus, a user can replace existing control modules with newer control modules that allow for a display having higher resolution or more color bit depth or 3D. Similarly, a user can replace an existing input module, which only supports a limited number of camera heads, without replacing the control module or the display.

Such a system provides a competitive advantage by being able to provide newer technologies faster and users the benefit of the backwards and forwards compatibility between the control modules and input modules.

The modular imaging system allows upgradeability and compatibility with a multitude of camera heads that are supported by a plurality of input modules, where the camera heads and input modules may be existing or yet to be developed. Formerly, when a new imaging technology became available, a CCU would not be incompatible with the new technology due to a variety of constraints, for example, outdated hardware. By using a modular architecture, the new technology can be supported by a new input module that is backward compatible with the existing control module. The modular architecture increases the likelihood that existing visualization technology and yet to be developed visualization technology will be able to operate with some if not all of the same image processing hardware. This results in decreased capital costs for physicians offices, surgical offices and/or hospitals.

The control module may be designed to accommodate general image processing and display functions. These general functions include, for example, supporting a separate user interface, overlaying a user interface onto an image, image capture and streaming functionality as well as input/output functionality for the display/monitor interfaces, system interface and control, and network connectivity. The control module may be designed to accommodate a single input module or multiple input modules. The control module may be connected to a display or the control module includes a display as a one piece unit. The control module may include a processor as well.

For example, a user may only wish to purchase a control module and only one input module at a time. Thus, the overall modular system can be purchased at a lower initial cost. If the consumer wishes to purchase a new camera type, the modular system can be upgraded with a new input module to support the new imaging technology. The new input module may replace the old input module or be used together with the older input module.

The input modules can support functions required for a group or family of image sources, such as cameras or auxiliary inputs. The input module can provide compatibility between the family of image sources and the control module. Over the life of the system, additional input modules may be purchased to support emerging imaging technology such as 3D imaging, advanced fluorescence imaging, solid-state variable direction of view endoscopes, wireless camera heads and so on.

The group of input modules connected to the control module may include an auxiliary input module. The auxiliary input module may support a variety of video sources such as third party camera control units, C-Arm, X-Ray, Ultrasound, Personal Computers and the like. Supported input formats may include, DVI, VGA, S-Video, Composite, 3G-SDI and the like. Inputs may be both automatically and manually selected. The auxiliary module provides increased backward compatibility, forward compatibility and third party image source compatibility.

The control module and input modules may each have one or more power supplies. The control module can manage the ON/OFF power state of each input module connected to the control module. The control module may control the power state of the input modules by sending a signal to a power circuit in the input module, which controls the ON/OFF power state of the input module. The ON/OFF power state of the control module may dictate the ON/OFF power state of the connected input modules. For instance, if the control module is OFF the control module may put each connected input module into an OFF power state. Further, if the control module if ON the control module may put each connected input module into an ON power state. The input modules may have a default ON power state when not connected to a control module. The input modules may be able to be connected and disconnected to the control module without damaging the system and automatically resume normal operation.

It should be noted that as used herein, the categorization of Standard Definition (SD) or High Definition (HD) is not intended to limit the categories to a single signal format, but rather, many differing signal formats may be used. Furthermore, many different signal formats are categorized as SD and many different signal formats may be categorized as HD. For instance, SD generally refers to a line count of up to approximately 720×480 NTSC and PAL; while HD refers to systems that utilize a higher line count and may include, but is not limited to, 1280×720 progressive or 1920×1080 interlaced, which are only two of the commonly used HD resolutions. Furthermore, the modules are capable of sending digital video in the form of HD and SD video over the cable from module to module at fully run-time programmable image sizes, color spaces, bit-depths and frame-rates. The receiving and transmitting ends of the video signals can auto-negotiate these various parameters.

There are commonly used types of signal formats, however, it is contemplated that additional formats may be provided for and especially new signal formats that may become available. Two commonly used SD format types are NTSC and PAL. It should be noted that these are just two video signal formats and that there are many differing types and modifications to the above-listed types including, for example, a modified version Phase-Alternating Line (PAL-M).

In addition to the standard NTSC and PAL SD (NTSC and PAL) composite, RGB, and s-video (Y/C) outputs, numerous other outputs may be used. The following examples are presented to further illustrate and explain the present invention and should not be taken as limiting in any regard.

Serial Digital Interface (SDI), standardized in ITU-R BT.656 and SMPTE 259M, is a digital video interface used for broadcast-grade video. A related standard, known as High Definition Serial Digital Interface (HD-SDI), is standardized in SMPTE 292M and provides a nominal data rate of 1.485 Gbit/s.

Digital Visual Interface (DVI) is a video interface standard designed to maximize the visual quality of digital display devices such as flat panel LCD computer displays and digital projectors and is partially compatible with the HDMI standard in digital mode (DVI-D). The DVI interface uses a digital protocol in which the desired illumination of pixels is transmitted as binary data. When the display is driven at its native resolution, it will read each number and apply that brightness to the appropriate pixel. In this way, each pixel in the output buffer of the source device corresponds directly to one pixel in the display device.

High-Definition Multimedia Interface (HDMI) is an all-digital audio/visual interface capable of transmitting uncompressed streams. HDMI is compatible with High-bandwidth Digital Content Protection (HDCP) Digital Rights Management technology. HDMI provides an interface between any compatible digital audio/video source and a compatible digital audio and/or video monitor, such as a digital television (DTV).

The modular architecture of the present system allows for easy power control of the entire system. The modular architecture also allows economical buyers to progressively upgrade their imaging technology, rather than being required to purchase a CCU that is compatible with the entire range of imagers that the buyer would wish to purchase in the future. The system allows for hardware upgrades through the modules as well as software feature upgrades. Further, the cost of ownership and upgrade, such as acquisition, back-up, and maintenance, is reduced.

Referring now to the drawings, wherein like reference numerals designate corresponding structure throughout the views.

FIG. 1A shows a perspective view of the endoscopic system 2000 including input modules 2200, 2300 and 2400, and the control module 2100 stacked upon one another. Control module 2100 is shown connected to display 3000. In certain embodiments, the control module 2100 may be separate from the display 3000 and in other embodiments the control module 2100 may form a one-piece unit with the display. In certain embodiments, the display has a screen 3050, which may be a touch screen. Control module 2100 is shown having an on/off switch 2102, which can control the power of all of the input modules 2200, 2300 and 2400.

Internal portions of input modules 2200, 2300 and 2400 are also shown in FIG. 1A. The processor 2142 for the control module 2100 and the processors, 2242, 2342 and 2442 for the input modules 2200, 2300, 2400 may controls the power status of the input modules. The processor 2142 for the control module 2100 may send control data 3500 (FIG. 1B) to the processors, 2242, 2342 and 2442 for the input modules 2200, 2300, 2400 to control each of the input modules power state.

The processor 2342 for input module 2300 may also convert image data 2204 received from the camera head 4000 into processed image data that is compatible with the control module 2100. Similarly, the processor 2242 for input module 2200 and the processor 2442 for input module 2400 may also convert image data into processed image data 2500 (FIG. 4) that is compatible with the control module 2100. It should be understood that the processors for sending control data and for converting image data may be integrated or separate. Furthermore, it should be understood that the control data may not be sent by a processor, but the control data may be a simple electrical signal, voltage or change in voltage from the control module.

Input modules 2200, 2300, and 2400 may be configured to receive and process numerous types of image data 2204. Image data 2204 may include analog data such as CCD based video endoscopes (⅙", ⅛" CCDs) (Pre-CDS analog); CMOS (post CDS analog); and/or 720p60 single chip Digital Proximal Heads (for smaller camera heads requiring less than 1080p resolution but better than Standard Definition (SD)). Image data 2204 may also be analog High Definition (HD) image data such as from 3-Chip HD CCD camera heads or digital HD image data such as from 1080p60 3chip camera heads (CMOS) or 1080p60 1chip camera heads (CMOS). Finally image data 2204 may also be advanced fluorescence imaging, solid-state variable direction of view endoscopes, wireless camera heads and so on.

The camera head 4000 is connected to input module 2300 by a cable 4500. Cable 4500 has a connector 4550 that connects into a slot such as shown in input module 2200 as slot 2250. Camera head 4000 may send image data 2204 to the input module through the cable 4500.

Figure 1B:
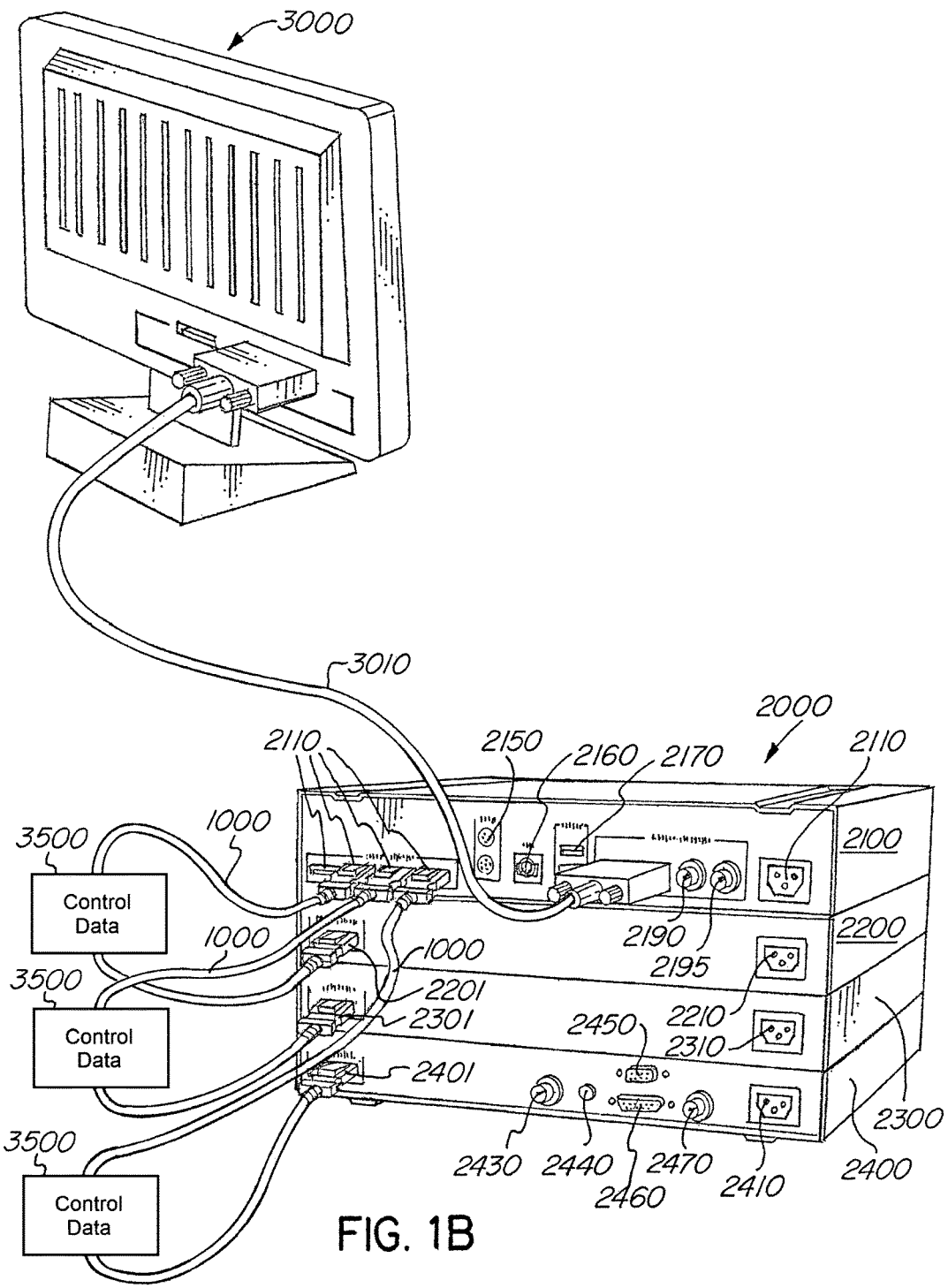
FIG. 1B is a rear perspective view of FIG. 1A.

FIG. 1B shows control module 2100 being connected to input modules 2200, 2300 and 2400 via cables 1000 and control data 3500 being transmitted between the control module 2100 and input modules 2200, 2300 and 2400. FIG. 1B also shows display 3000 connected to control module 2100 via cable 3010.

Figure 2:
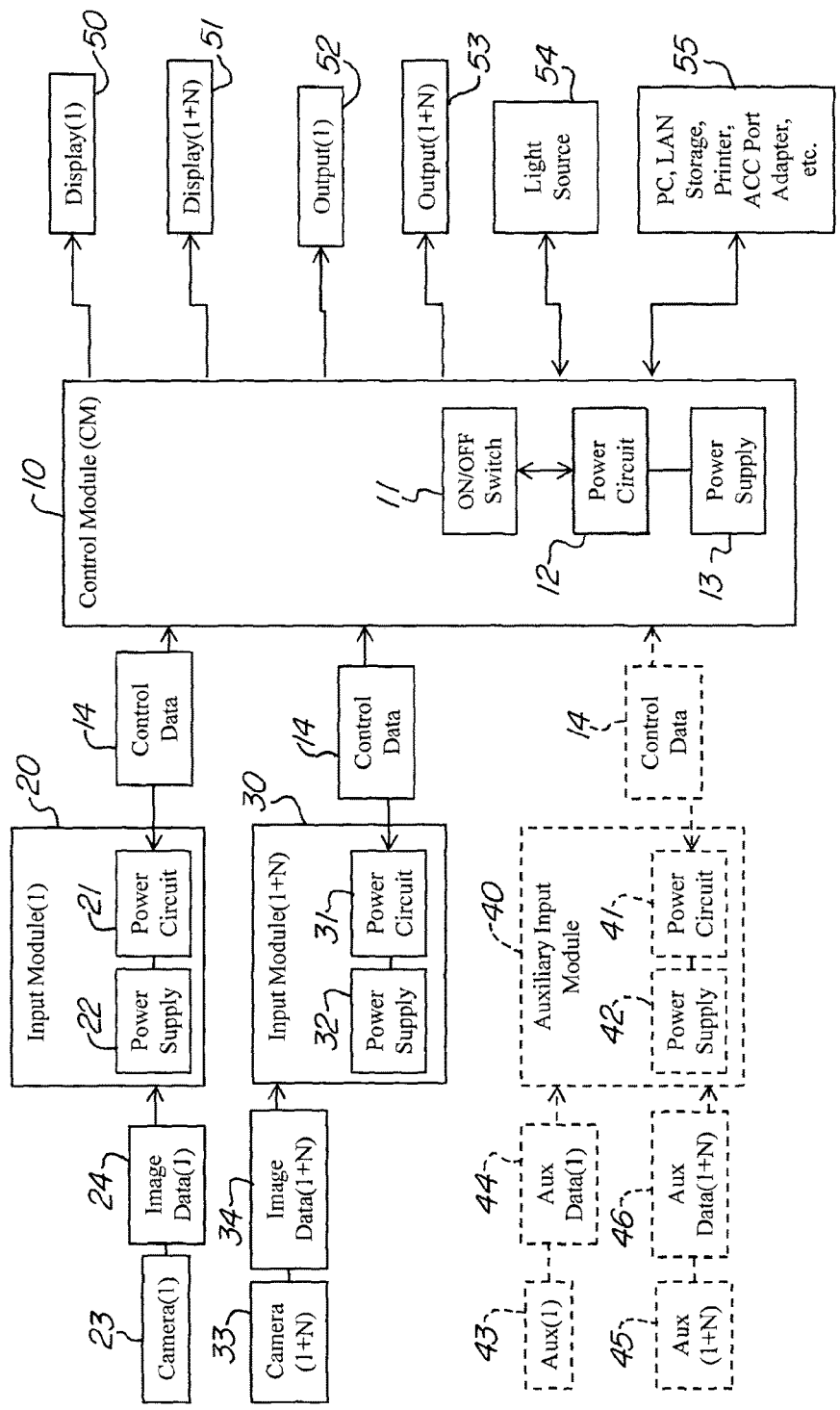
FIG. 2 is a schematic of the system in FIGS. 1A and 1B.

FIG. 1B shows input modules 2200, 2300 and 2400 each having a power plug 2210, 2310 and 2410 to be connected to a power source. Each input module may have one or more integral power supplies to support an ever increasing variety of camera heads and their unique power requirements. The control module 2100 is shown having four slots 2110 for receiving cables 1000 and the control module 2100 also has various connection elements 2150, 2160, 2170, 2190, and 2195 to connect to various other devices including input and output devices 55 (FIG. 2). Such input/output devices may include printers, external storage devices, personal computers, local area networks, light sources, keyboards, and/or ACC port adapters. Other example input/output elements may include DVI output for DVI monitors or recorders, 3G SDI outputs for 3G SDI monitors or recorders Input modules 2200, 2300 and 2400 each have a slot 2201, 2301, 2401 respectively for receiving the cable 1000 which transfers information between the input modules and the control module 2100, such as control data 3500 to control the power state of the input modules 2200, 2300 and 2400. Input module 2400 has various input and output elements 2430, 2440, 2450, 2460 and 2470 to connect to various other input and output devices. Such input/output devices may include existing or third-party CCUs, C-Arm, X-Ray, Ultrasound, and personal computers. Such inputs may also include DVI, VGA, S-Video, Composite, 3G-SDI. Other additional input and output elements may be envisioned for the various input modules 2200, 2300 and 2400.

FIG. 2 is a schematic of a modular medical imaging system that may be used, for example, in a hospital. The system has a control module 10 that can be connected to multiple input modules 20, 30, 40. Each input module 20, 30, 40 has its own power supply 22, 32, 42 and power circuit 21, 31, 41 for controlling the power status of the input modules 20, 30, 40. The control module 10 also has a power switch 11 and a power circuit 12 and power supply 13 connected to together. Control data 14 is sent between the control module 10 and the input modules 20, 30 and 40. The control data 14 provides control information including the connection state of the input modules 20, 30, 40 to the control module 10 and the power state of the input modules 20, 30, 40 and the control module 10.

The control module 10 manages the power state of the input modules 20, 30, 40. For example, input module(1) 20 has a power supply 22 connected to a power source and the power supply 22 is connected to a power circuit 21. The power circuit 21 controls the power state of the input module (1), or more specifically whether the input module(1) 20 is ON or OFF. The input module(1) 20 can be connected and disconnected to the control module 10 by a user. If the input module(1) 20 is disconnected from the control module 10 the power circuit 21 will not receive any control data 14 from the control module 10 indicating it is disconnected and the power circuit 21 will default the power condition to ON. Now if the input module(1) 20 is connected to the control module 10, the control module 10 will send the power circuit 21 in the input module(1) 20 control data 14 to manage the power state of the of the input module(1) 20. For instance, if the control module 10 is ON, the power circuit 12 of the control module 10 will send control data 14 to the power circuit 21 of the input module(1) 20 indicating that it is ON and the power circuit 21 will turn the input module(1) 20 ON. Now, if the control module 10 is OFF, the power circuit 12 of the control module 10 will send control data 14 to the power circuit 21 of the input module(1) 20 that indicating that the control module 10 is OFF and the power circuit 21 will turn the input module(1) 20 OFF.

The above control module 10 power management sequence works for all input modules 20, 30, 40 connected to the control module 10 regardless of how many input modules are connected to the control module 10. It should be understood that the power circuits and power supplies for the individual modules can be integrated or separate components. It should further be understood that the power circuits of the modules can be integrated with other components or circuitry of the individual module, such as the modules processor. It should be further understood that the power circuit could be software based. Finally, it should be understood that the power switch 11, power circuit 12 and power supply 13 of the control module 10 can also be separate, integrated together or integrated with other components.

The power supplies in the input and control modules can be any suitable power supply including a low voltage power supply. Also, the input and control modules may contain one or more power supplies in order to power various other components. For instance, as shown in the FIG. 2 the input modules can be connected to cameras, such as camera(1) 23 or camera(1+N) 33, which may be powered by the input modules 20, 30. Furthermore, if the input module is an auxiliary input module 40 it could be connected to several types of devices, such as Aux(1) 43 or Aux(1+N) 45, which may also need power from the auxiliary module. Finally, the control module 10 may also provide power to devices connected to it, such as displays 50, 51 or other type of output 52, 53. The control module may also provide power to a light source 54.

Figure 3:
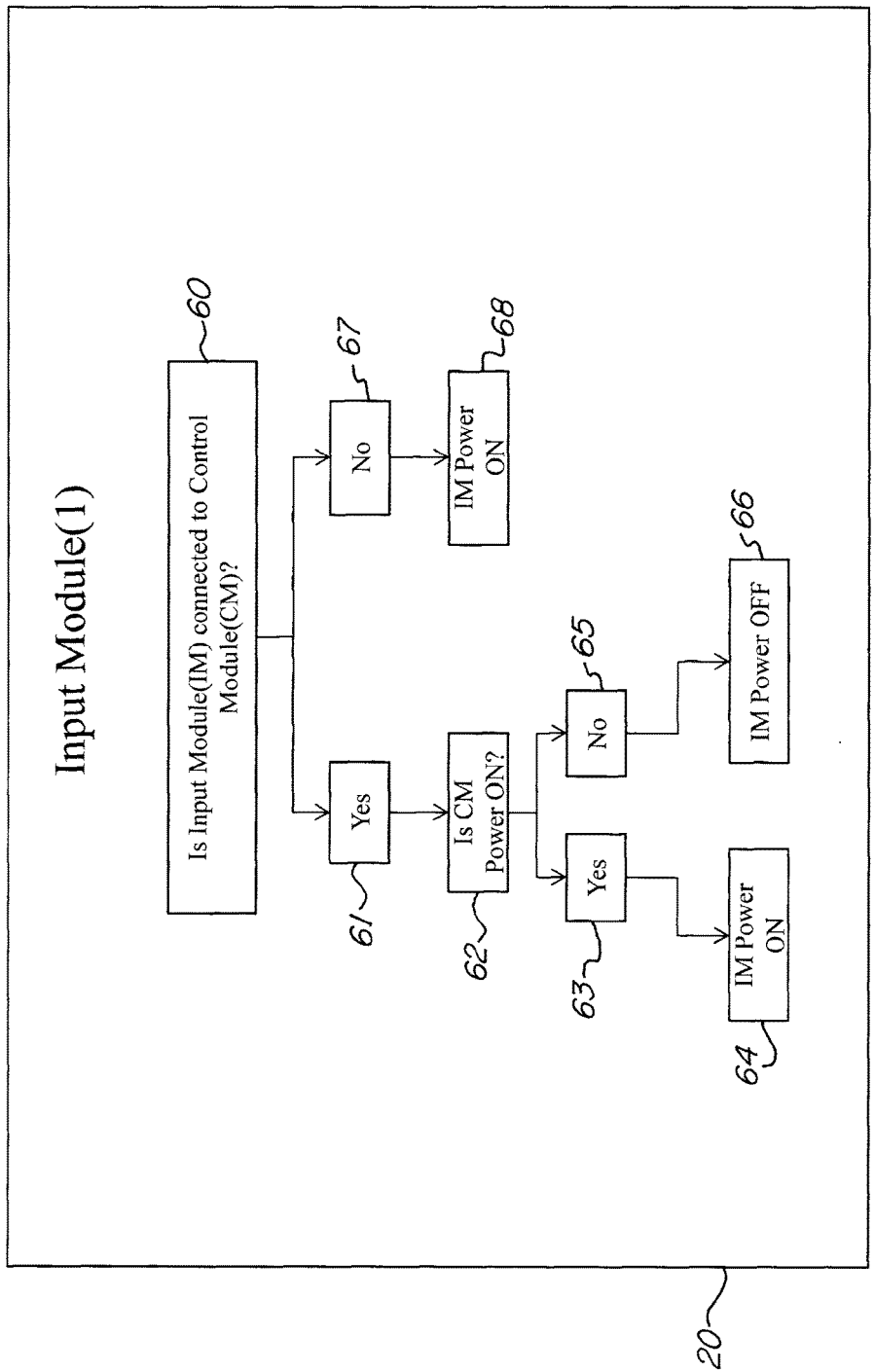
FIG. 3 is a flow chart showing the power management of an input module.

FIG. 3 is a flow chart of an operating scheme of the input module(1) 20. It should be understood that this operating scheme can be utilized by all the input modules connected to the control module. As shown in FIG. 3, the input module first determines whether the input module is connected to the control module 60. If the input module is not connected to the control module 67, the input module defaults to a powered ON state 68. If the input module is connected to the control module 61, the input module must then determine if the control module is ON or OFF 62. If the control module power is ON 63, then the input module will enter a powered ON state 64. If the control module is OFF 65, then the input module will enter a powered OFF state 66.

By the input module defaulting to a powered ON state 68, the input module can be connected and disconnected to the control module without powering OFF. This functionality allows for input modules to be connected and disconnected on the fly, which allows different modules to be swapped into the system without needing to wait for them to power ON. This also prevents the input modules from powering OFF if accidently disconnected.

Figure 4:
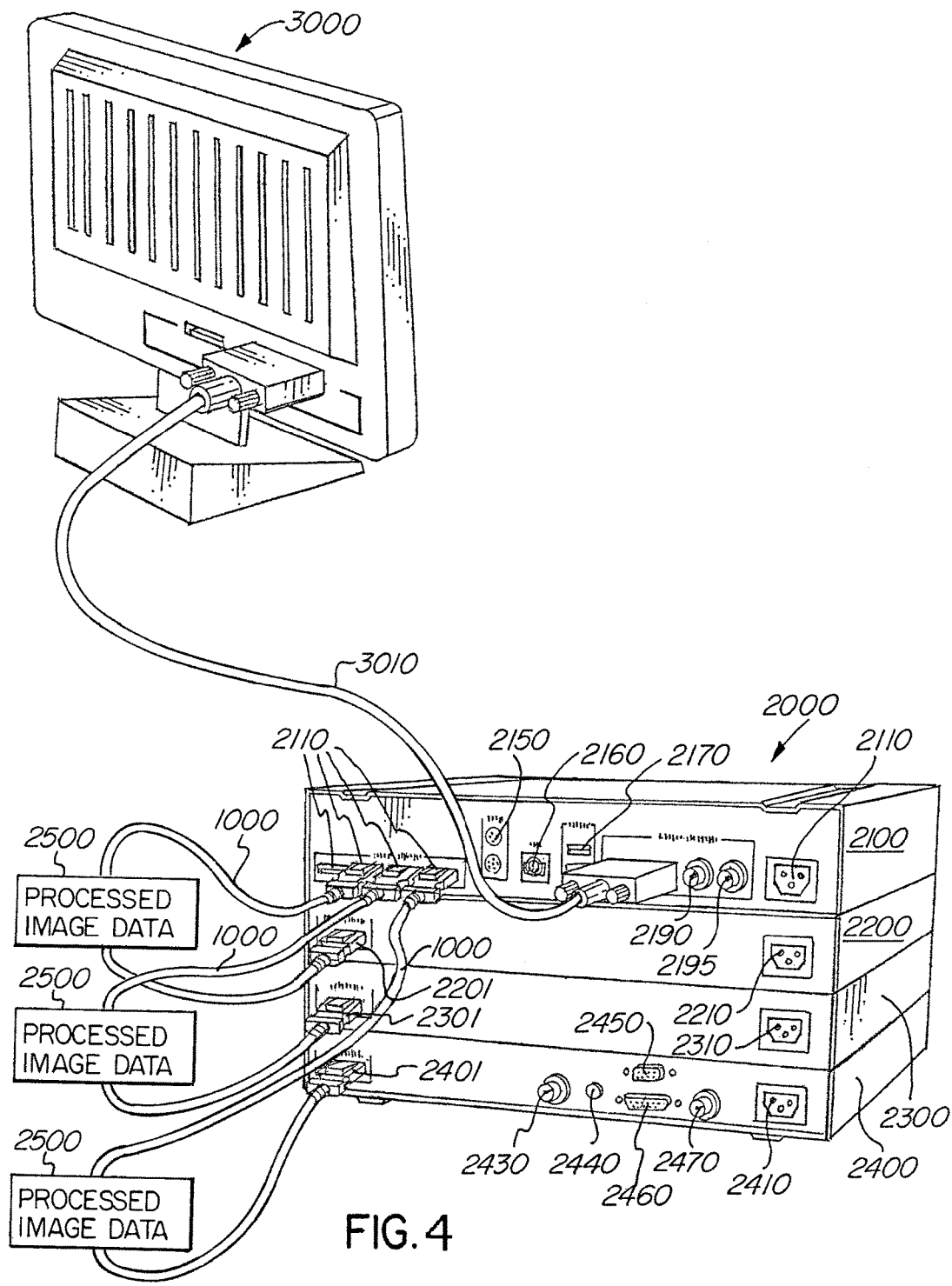
FIG. 4 is a rear perspective view of FIG. 1A.

FIG. 4 shows the cable 1000 can also transfer processed image data 2500 between the input modules and the control module 2100. The processed image data 2500 may be sent over different wires in the cable 1000 than the control data 3500 or the same wires. It should also be understood that both the processed image data 2500 and control data 3500 may be transmitted wirelessly between the input modules and the control module.

Figure 5:
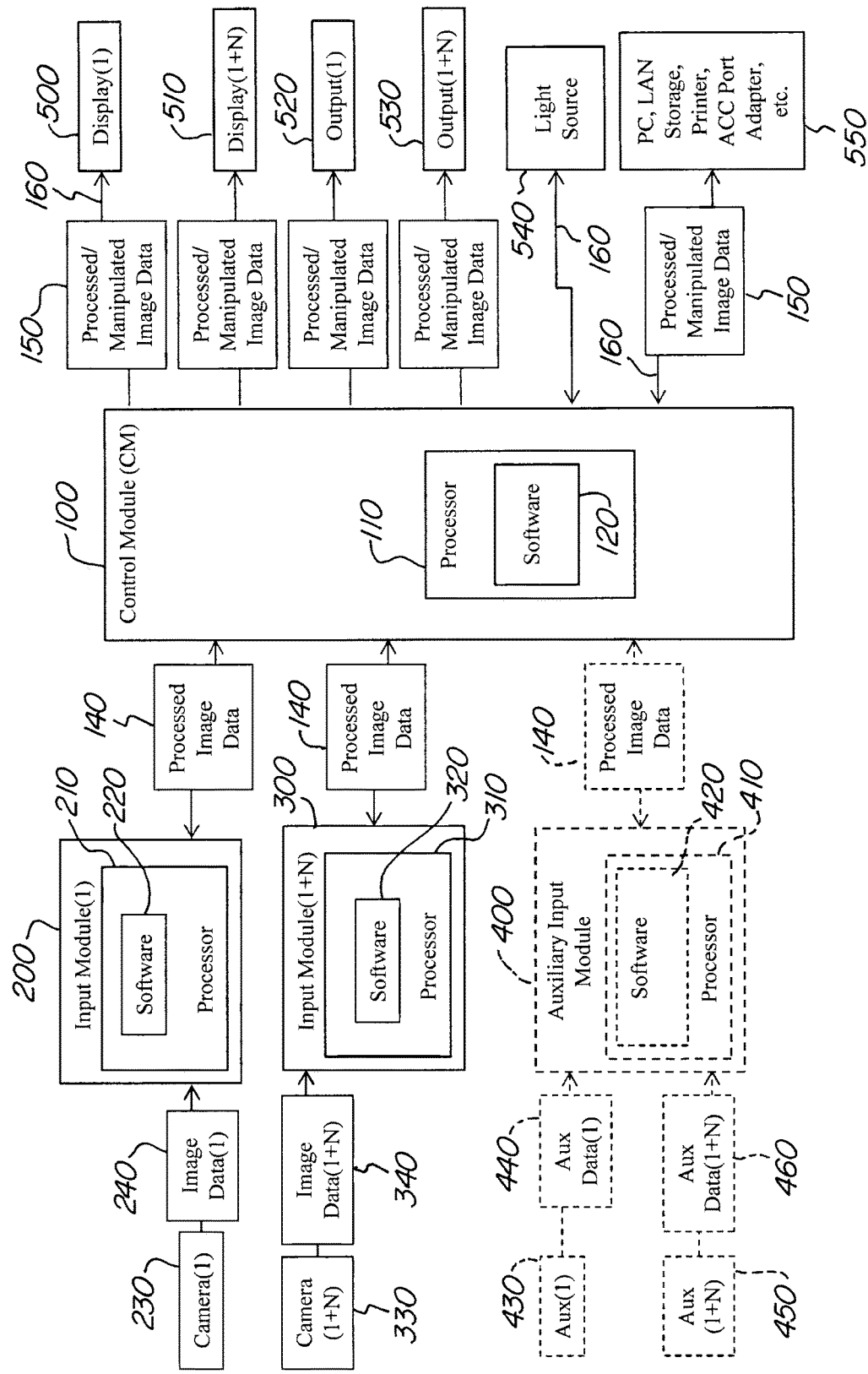
FIG. 5 is a schematic of the system in FIG. 4.

FIG. 5 is a schematic of a modular medical imaging system. The system has a control module 100 that can be connected to multiple input modules 200, 300, 400 that support different types of image data 240, 340, 440, 460 and process the image data 240, 340, 440, 460 into processed image data 140 which is a format compatible with the control module 100. The control module then provides functions not specific to the image data 240, 340, 440, 460 such as general image processing and outputs processed and/or manipulated image data 150 to a display/output 500, 510, 520, 530, 550.

More specifically, in this system camera(1) 230 and camera(1+N) 330 output different types of image data, image data(1) 240 and image data(1+N) 340 respectively. Therefore, input module(1) 200 receives image data(1) 240 and processes it into processed image data 140 to be sent to the control module 100. Camera(1+N) 330 is not compatible with input module(1) 200 so it is connected to input module (1+N) 300, which supports image data(1+N) 340. Input module(1+N) 300 receives image data(1+N) 340 and processes it into processed image data 140 to be sent to the control module 100.

It should be understood that input module 200, 300, 400 can be configured to receive multiple types of image data. Furthermore, image data may be for a single type of camera or a family of cameras. It should also be understood that the input modules may process the image data through hardware or software or some combination of hardware and software. For instance, input module(1) can implement a processor 210 running software 220 to process image data(1) 240 into processed image data 140. Similarly, input module(1+N) can implement a processor 310 running software 320 to process image data(1+N) 340 into processed image data 140.

The system may also implement an auxiliary input module 400, which can support multiple auxiliary devices. In this case, Aux(1) 430 outputs Aux Data(1) 440 that is received by the auxiliary input module 400 and processed into processed image data 140. Aux(1+N) 450 outputs aux data(1+N) 460 that is received by the auxiliary input module 400 and processed into processed image data 140. It should also be understood that the auxiliary input module 400 may process the image data through hardware or software or some combination of hardware and software. In one embodiment, auxiliary input module 400 can implement a processor 410 running software 420 to process image data 440, 460 into processed image data 140.

It should be under stood that terms input module and auxiliary input module can be used interchangeably as the purpose of the input/auxiliary modules is to process differing types of image data into a standard format for the control module 100. It should also be understood that while FIG. 5 shows each input module 200, 300, 400 being connected to the control module 100 with a cable 130, that the input modules and control module 100 can be wirelessly connected.

Control module 100 receives processed image data 140 from either all or some of the input modules 200, 300, 400 and can carry out general image processing, user interface and connect with various outputs. For instance, the control module 100 can connect to a touch screen display which provides a user interface through with to control the module. The control module can further process the processed image data 140 and transmit the process/manipulated image data 150 to various places, such as displays 500, 510, outputs 520, 530, PCs, LANs, Storage devices, printers, ACC Port Adapters 550, etc. The process/manipulated data 150 can be any combination of processed and/or manipulated data. Manipulation to the data can include overlaying a graphical user interface (GUI) on an image, zooming in on an image, and picture-in-picture of multiple sources including from other input modules. Manipulation to the data may also include image rotation, perspective correction, cropping, pan and scan, tilt and mirror in the horizontal and the vertical direction, and correcting for endoscope artifacts.

The control module 100 may also be configured to provide artificial horizon, wide angle lens support, adoption of camera perspective to surgeon perspective, intelligent image pan/scan controlled via surgeon movement.

It should be understood that the control module 100 may further process the process the image data 140 through hardware or software or some combination of hardware and software. For instance, control module 100 can implement a processor 110 running software 120 to further process the processed image data 140 into manipulated image data 150.

In order to be backwards and forwards compatible the control module 100 and input modules 200, 300, 400 may have to communicate what types of standard processed image data 140 they are compatible with. For instance, control module 100 may be compatible with several types of standard processed image data (e.g. HD or SD) and may have to communicate this compatibility with each input modules 200, 300, 400 in turn the input modules may have to communicate what types of standard processed image data 140 they are capable of transmitting. By communicating this information between the control module 100 and each input module 200, 300, 400 can settle on a type of standard processed image data 140 to communicate. Such functionality allows for the use of newer control modules with older input modules and newer input module with older control modules. For instance, if an input module was made for a newer imaging technology (e.g. HD) the input module may be capable of transmitting processed image data in HD or SD formats so that the new HD input module could function with an older SD control module. Likewise, if a user had a newer HD control module, the control module would be able to receive both HD and SD image data such that the HD control module would be backwards compatible with SD input modules.

In certain embodiments, the control module 100 is connected to, for example, an Intranet, the Internet and/or the like. In certain embodiments, the input modules 200, 300, 400 and/or the control module 100 includes WI-FI and/or a way to receive information directly from the Internet, either wired or wirelessly. In certain embodiments, any of the input modules may wirelessly connect to a related camera.

In certain embodiments, upon connection of control module 100 to, for example, input module 200 an input module identifier/program stored on input module 200 may be transmitted to the control module. It is contemplated that the input module identifier may comprise discrete data or may comprise a program that provides information relating to the input module 200 to the control module 100. In addition, it is contemplated that the control module 100 may also transmit a control module identifier/program stored on the control module 100 to the input module 200. It is contemplated that the control module identifier may comprise discrete data or may comprise a program that provides information relating to the control module 100 to the input module 200.

In certain embodiments, the control module 100 may send commands to the input module 200, which may include, for example, adjusting color balance, light, focal distance, resolution, zoom, focus, shading, and other optical characteristics if the input is a camera video or video endoscope. Input module 200 may then generate and transmit processed image data 140 to control module 100.

While the invention has been specifically described in connection with certain specific embodiments thereof, it is to be understood that this is by way of illustration and not of limitation, and that various changes and modifications in form and details may be made thereto, and the scope of the appended claims should be construed as broadly as the prior art will permit.

The description of the invention is merely exemplary in nature, and, thus, variations that do not depart from the gist of the invention are intended to be within the scope of the invention. Such variations are not to be regarded as a departure from the spirit and scope of the invention.

What is claimed is:

1. A modular medical video imaging system, comprising:
a control module having an on condition;
at least one input module having an on condition and an off condition;
a communication link placing said control module and said at least one input module in signal communication;
said at least one input module being in the on condition when said at least one input module receives an on signal from said control module over said communication link indicating that said control module is in the on condition; and
said at least one input module being in the off condition when said at least one input module receives an off signal from said control module over said communication link indicating that said control module is not in the on condition;
wherein said at least one input module has a disconnected state from said control module, said at least one input module configured to default to the on condition when said at least one input module is in the disconnected state from said control module.

2. The modular medical video imaging system of claim 1, wherein said communication link is a cable, said cable including a first set of wires allowing for image data to be transmitted across the cable and a second set of wires for the on signal and the off signal to be transmitted across the cable.

3. The modular medical video imaging system of claim 1, wherein said communication link is a wireless communication link.

4. The modular medical video imaging system of claim 1, wherein said control module further comprises:
a power switch with an on position and an off position;
said on position putting said control module into said on condition.

5. The modular medical video imaging system of claim 1, wherein said control module has at least one power supply and said at least one input module has at least one power supply.

6. The modular medical video imaging system of claim 5, wherein the at least one power supply of said control module can power said control module and a device.

7. The modular medical video imaging system of claim 6, wherein the device is light source.

8. The modular medical video imaging system of claim 5, wherein the at least one power supply of said at least one input module can power said at least one input module and a device.

9. The modular medical video imaging system of claim 7, wherein the device is an endoscope.

10. A modular medical video imaging system, comprising:
a control module having an on condition and an off condition;
at least one input module having an on condition and an off condition, said at least one input module having a disconnected state from said control module;
a communication link to place said at least one input module into a connected state to said control module
a control signal communicated from said control module to said at least one input module when said at least one input module is in said connected state to said control module, said control signal communicating whether said control module is in the on condition or the off condition;
said at least one input module being in the on condition when said at least one input module receives said control signal indicating that said control module is in the on condition;
said at least one input module being in the off condition when said at least one input module receives said control signal indicating that said control module is in the off condition; and
said at least one input module configured to default to the on condition when said at least one input module is in the disconnected state from said control module.

11. The modular medical video imaging system of claim 10, wherein said at least one input module is configured to be disconnected and connected to said control module when said control module is in the on condition without said at least one input module entering the off condition.

12. The modular medical video imaging system of claim 10, wherein said communication link is a cable for connecting said control module and said at least one input, said cable including a first set of wires allowing for video data to be transmitted across the cable and a second set of wires for said control signal to be transmitted across the cable.

13. The modular medical video imaging system of claim 10, wherein said communication link is a wireless communication link.

14. The modular medical video imaging system of claim 10, wherein said control module further comprises:
a power switch with an on position and an off position;
the on position putting said control module into the on condition; and
the off position putting said control module into the off condition.

15. The modular medical video imaging system of claim 10, wherein said control module has at least one power supply and said at least one input module has at least one power supply.

16. The modular medical video imaging system of claim 15, wherein the at least one power supply of said control module can power said control module and a device.

17. The modular medical video imaging system of claim 16, wherein the device is light source.

18. The modular medical video imaging system of claim 13, wherein the at least one power supply of said at least one input module can power said at least one input module and a device.

19. The modular medical video imaging system of claim 18, wherein the device is an endoscope.

20. A method for providing a modular video imaging system, the method comprising the steps of:
providing a control module having an on condition;
providing at least one input module having an on condition and an off condition;
placing said control module and said at least one input module in signal communication via a communication link;
when said at least one input module is in the on condition, transmitting an on signal from said control module over said communication link, and receiving said on signal by said at least one input module, said on signal indicating that said control module is in the on condition; and
when said at least one input module is in the off condition, transmitting an off signal from said control module over said communication link, and receiving said off signal by said at least one input module, said off signal indicating that said control module is not in the on condition;
wherein said at least one input module has a disconnected state from said control module, said input module configured to default to the on condition when said at least one input module is in the disconnected state from said control module.

* * * * *